US012633385B2

(12) United States Patent
Goldstein et al.

(10) Patent No.: US 12,633,385 B2
(45) Date of Patent: May 19, 2026

(54) SYSTEMS AND METHODS FOR SECURELY SHARING ELECTRONIC HEALTH INFORMATION

(71) Applicant: MEDICOM TECHNOLOGIES INC., Raleigh, NC (US)

(72) Inventors: Brent Goldstein, Raleigh, NC (US); Malcolm Benitz, Raleigh, NC (US); Chase Ballard, Raleigh, NC (US); Michael Rosenberg, Raleigh, NC (US)

(73) Assignee: Medicom Technologies, Inc., Raleigh, NC (US)

( * ) Notice: Subject to any disclaimer, the term of this patent is extended or adjusted under 35 U.S.C. 154(b) by 775 days.

(21) Appl. No.: 17/488,201

(22) Filed: Sep. 28, 2021

(65) Prior Publication Data

US 2022/0101966 A1     Mar. 31, 2022

Related U.S. Application Data

(60) Provisional application No. 63/198,070, filed on Sep. 28, 2020.

(51) Int. Cl.
*G16H 10/60* (2018.01)
*G06N 20/00* (2019.01)
*G16H 50/70* (2018.01)

(52) U.S. Cl.
CPC ............. *G16H 10/60* (2018.01); *G06N 20/00* (2019.01); *G16H 50/70* (2018.01)

(58) Field of Classification Search
None
See application file for complete search history.

(56) References Cited

U.S. PATENT DOCUMENTS

| | | | |
|---|---|---|---|
| 8,108,228 B2 * | 1/2012 | Maresh ................. | G16H 40/67 705/3 |
| 2008/0133273 A1 * | 6/2008 | Marshall ............... | G06Q 10/10 705/3 |
| 2010/0033762 A1 * | 2/2010 | Mickeleit ............. | G06F 3/1247 358/1.15 |
| 2010/0228559 A1 * | 9/2010 | Boone ................... | G06Q 10/06 358/1.15 |
| 2010/0268552 A1 * | 10/2010 | Schoenberg ........... | G06Q 10/10 705/34 |
| 2012/0060216 A1 * | 3/2012 | Chaudhri ............... | G06Q 10/10 726/21 |
| 2013/0304510 A1 * | 11/2013 | Chen ...................... | G16H 10/60 705/3 |
| 2015/0100787 A1 * | 4/2015 | Westin ............... | H04L 63/0414 713/168 |
| 2015/0347685 A1 * | 12/2015 | Dutta .................. | H04L 63/0428 705/51 |

(Continued)

*Primary Examiner* — Mamon Obeid
*Assistant Examiner* — Andrew Kyle Tapia

(57) ABSTRACT

The present invention relates, in general, to systems and methods that allow medical providers to electronically share medical data with other providers, and where the medical data is organized or classified upon receipt using mapping and/or machine learning techniques. The present invention further facilitates clinical decision support functions such as appropriate use assessments, treatment decision-making, pharmaceutical research support functions, as well as clinical trial qualification functions.

20 Claims, 3 Drawing Sheets

(56)        References Cited

U.S. PATENT DOCUMENTS

| | | | |
|---|---|---|---|
| 2016/0098523 A1* | 4/2016 | Laskin | G16H 10/60 |
| | | | 705/3 |
| 2016/0147954 A1* | 5/2016 | Ng Tari | G16H 40/20 |
| | | | 705/3 |
| 2016/0217347 A1* | 7/2016 | Mineo | A61B 5/441 |
| 2018/0284758 A1* | 10/2018 | Cella | G06N 3/088 |
| 2020/0043577 A1* | 2/2020 | Jiang | G16H 10/60 |
| 2020/0176098 A1* | 6/2020 | Lucas | G06F 40/30 |
| 2020/0350072 A1* | 11/2020 | McEwing | G16H 50/70 |
| 2020/0409613 A1* | 12/2020 | Lankreijer | G06F 3/1263 |
| 2021/0012892 A1* | 1/2021 | Nagura | G06F 3/14 |
| 2021/0319859 A1* | 10/2021 | Reumann | G16H 10/60 |

* cited by examiner

SYSTEMS AND METHODS FOR SECURELY SHARING ELECTRONIC HEALTH INFORMATION

CROSS-REFERENCE TO RELATED APPLICATION

This application claims the benefit of U.S. Provisional Patent Application No. 63/198,070 entitled "SYSTEMS AND METHODS FOR SECURELY TRANSMITTING HEALTHCARE INFORMATION" filed on Sep. 28, 2020, which is commonly owned, the disclosure of which is incorporated herein by reference in its entirety.

BACKGROUND

Field of the Invention

The present invention relates, in general, to systems and methods that allow medical providers to electronically share medical data with other providers, and where the medical data is organized or classified upon receipt using mapping and/or machine learning techniques. The present invention further facilitates clinical decision support functions such as appropriate use assessments, treatment decision-making, pharmaceutical research support functions, as well as clinical trial qualification functions.

Description of Related Art

Transmission of medical data is complicated by the fact that they are subject to Health Insurance Portability and Accountability Act of 1996 ("HIPAA") requirements, whereby all entities that take possession of such studies, even when ephemeral, must be pre-qualified as HIPAA compliant. One solution to this problem is to establish a virtual private network ("VPN") between the medical provider and the diagnostic lab. However, this solution suffers from complexity and cost. Installing a VPN between two providers commonly means segregating the network at both ends to limit what each of the other parties can see. While doing this between a single set of providers may seem straightforward, it quickly become less tractable when a single provider needs to communicate over VPN with a plurality of other providers. This requires creating a separate zone for each of the provider, and requires installing, configuring, and managing a separate VPN for each provider. As a result, scalability problems quickly arise as medical practices, patients, and throughout grows.

Another popular method of transmitting the medical data is to store it on a CD, DVD, or other media and physically shipping the media via postal mail, couriers, and/or messenger services. In some extreme cases, CDs are taped to patients as they are leaving one facility and in-route to another, or the CD is simply dropped into a patient stretcher, unsecured and prone to loss and damage.

In previous years, when communication and data networks were generally much slower, and bandwidth was limited and costly, such antiquated methods held appeal. However, physical media suffers from lack of immediacy given that it is generally quicker to send data over today's networks than to suffer the delays and risks involved in physical transit. Physical media is also prone to being damaged, stolen, or lost in transit, and inherently carries the risk of accidental or unwanted exposure of patient information and records.

Another solution to this problem medical is transmitting medical data using traditional fax or electronic fax services. For example, a medical provider who is seeking medical records or placing an order for an examination, procedure, or treatment for a patient typically manually generates a request and sends the request via fax to an external medical provider. Upon receipt by the external medical provider, the request is manually reviewed and processed by the recipient's staff.

What is needed is a system that is quick and easy to install and configure, complies with all regulations regarding privacy and security, provides for immediate delivery of medical data with confirmation and traceability, and includes a level of automation to alleviate manual burdens placed on medical staff. As such, the present invention empowers medical providers to share medical data efficiently and securely across a trusted network, which ultimately facilitates the preservation of the continuum of care for patients.

SUMMARY

In an embodiment, the invention relates to a system for sharing medical data, comprising: a first server affiliated with a first medical provider, the first server executing a printer driver; and a second server affiliated with a second medical provider, the second server including a print location associated with the printer driver; wherein the first server is programmed to: (i) retrieve medical data from a database coupled to the first server, (ii) generate a printable file that contains the medical data, and (iii) transmit the printable file to the print location via the printer driver, wherein the second server is programmed to: (i) receive the printable file at the print location, (ii) extract the medical data from the printable file, and (iii) format the medical data.

In another embodiment, the invention relates to a system for sharing medical data, comprising: a first server affiliated with a first medical provider, the first server executing a printer driver; and a second server affiliated with a second medical provider, the second server including a print location associated with the printer driver; wherein the first server is programmed to: (i) retrieve medical data from a database coupled to the first server, (ii) generate a printable file that contains the medical data, and (iii) transmit the printable file to the print location via the printer driver, wherein the second server is programmed to: (i) receive the printable file at the print location, (ii) temporarily store the printable file in a staging area, (ii) extract the medical data from the printable file, (iii) format the medical data, and (iv) store the formatted medical data in a location different from the staging area.

In yet another embodiment, the invention relates to a system for sharing medical data, comprising: a first server affiliated with a first medical provider, the first server executing a printer driver; and a second server affiliated with a second medical provider, the second server including a print location associated with the printer driver; wherein the first server is programmed to: (i) retrieve medical data from a database coupled to the first server, (ii) generate a printable file that contains the medical data, and (iii) transmit the printable file to the print location via the printer driver, wherein the second server is programmed to: (i) receive the printable file at the print location, (ii) temporarily store the printable file in a staging area, (iii) extract an identifier from the printable file, (iv) extract the medical data from the printable file, (v) format the medical data based on the identifier, and (vi) store the formatted medical data in a location different from the staging area.

BRIEF DESCRIPTION OF THE DRAWINGS

These and other embodiments of the disclosure will be discussed with reference to the following exemplary and non-limiting illustrations, in which like elements are numbered similarly, and where.

DEFINITIONS

Figure 1:
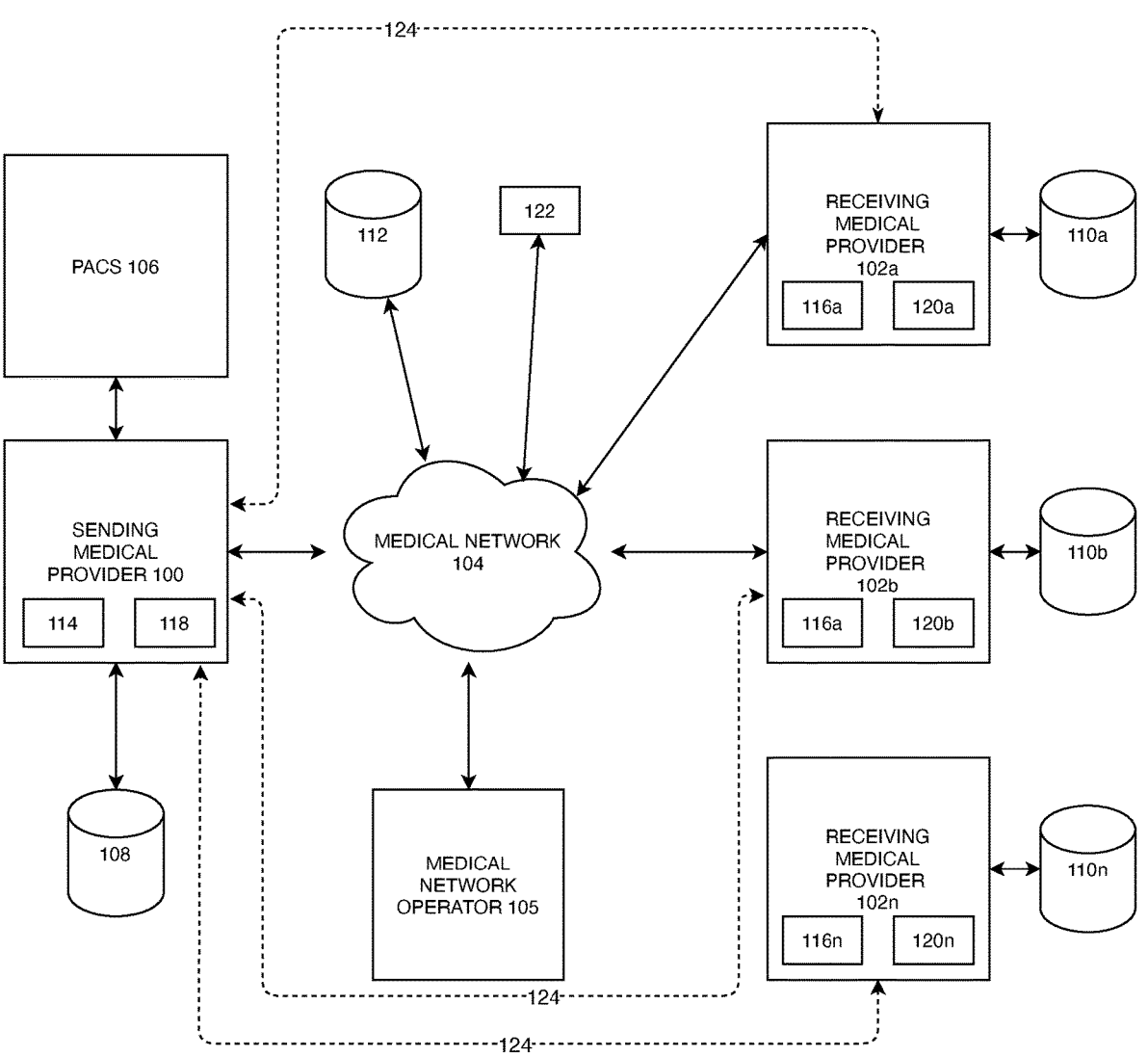
FIG. 1 is a network architecture diagram of a system for transmitting and fulfilling medical data requests across disparate medical providers, according to an embodiment of the invention.

The following definitions are meant to aid in the description and understanding of the defined terms in the context of the present invention. The definitions are not meant to limit these terms to less than is described throughout this application. Such definitions are meant to encompass grammatical equivalents.

As used herein, the term "medical data" can refer to, for example, any patient data, patient charts, electronic or paper medical records, medical imaging studies, medical and diagnostic images, diagnostic reads and reports, diagnostic notes, medical opinions, medical test and laboratory results, surgical history, family medical histories, medication lists, medical allergies, social histories and habits (such as, for example, drug, tobacco and alcohol use), immunization histories, clinical information, growth and development histories, medical encounter histories, physical examination observations, medical progress notes, dietary information, fitness and activity data, travel history, contact tracing records, medical orders, allergen information, insurance documents, clinical trial and research documents, and the like.

As used herein, the term "provider" can refer to, for example, a physician (including, but not limited to, a radiologist, surgeon, primary care physician, and a medical specialist), a physician assistant, a nursing professional, a medical laboratory technician, medical clinics, hospitals, health insurance providers, diagnostic sites, imaging sites, pharmacies, practice administrators, Medical Imaging Management staff, and the like. A "provider" can further be an individual patient, an academic institution, a government research laboratory, a non-profit entity, or a for-profit entity, such as a pharmaceutical, health insurance, biotechnology, wearable device, physiological monitoring, or medical device company.

As used herein, the term "data exchange interface" can refer to, for example, an interface, standard, specification and/or protocol that allows for disparate systems to share data, including, but not limited to, the Health Level Seven (HL7) standard, the Fast Healthcare Interoperability Resources (FHIR) standard, the HPRIM standard, the Continuity of Card Record (CCR) standard, the Continuity of Care Document (CCD) specification, the xDT data exchange format, the Arden syntax, an application programming interface (API), and direct access protocols for electronic health records systems, and the like.

As used herein, the term "PHI" can refer not only to protected health information, but also to PII and any other information that may be consider private, confidential, personally identifying, financial information, and the like.

As used herein, the term "machine learning" can refer to various artificial intelligence mechanisms and algorithms, including, but not limited to, reinforcement learning, predictive analytics, neural network analysis, fuzzy logic analysis, supervised and unsupervised learning functions, self-learning, deep learning, support-vector machine learning, and the like.

As used herein, the term "health information systems" can refer to an electronic health record (EHR) management systems, electronic medical record (EMR) systems, radiology information systems (RIS), picture archiving and communication systems (PACS), Digital Imaging and Communications in Medicine (DICOM) archives, a vendor neutral archive (VNA), a physician referral system, a laboratory testing ordering system, and any other medical and/or patient archive or database.

DETAILED DESCRIPTION

It should be understood that aspects of the invention are described herein with reference to the figures, which show illustrative embodiments. The illustrative embodiments herein are not necessarily intended to show all embodiments in accordance with the invention, but rather are used to describe a few illustrative embodiments. Thus, aspects of the invention are not intended to be construed narrowly in view of the illustrative embodiments. In addition, although the invention is described with respect to its application for the transfer of medical data, it is understood that the system could be implemented in any setting where the transfer of any type or form of sensitive, confidential, private, and/or personally identifying data may be useful.

FIG. 1 is a network architecture diagram of a system for transmitting and fulfilling medical data requests across disparate medical providers, according to an embodiment of the invention. In an embodiment, a sending medical provider 100 is communicatively coupled to at least receiving medical provider 102 via a medical network 104. The medical network 104 can be a restricted network operated by a medical network operator 105, such that the medical providers 100, 102 are registered with the medical network 104, and have a relationship with the medical network operator 105. Any medical providers who are not registered with the medical network 104 cannot access the medical network 104.

The term "receiving medical provider" as used herein refers to a medical provider which receives electronic medical requests. It is noted that a receiving medical provider can also be a sending medical provider, and vice versa, and the medical providers are also referred to as an "ordering medical provider" herein.

In an embodiment, the medical network 104 includes computing hardware, software, and/or services that facilitate the searching of medical records associated with the medical providers 100, 102. In an embodiment, the medical network 104 is configured as a server, local server, or a distributed server that can store data, as well as execute programs, algorithms, scripts, and applications.

In an embodiment, the medical network 104 is a proprietary network that facilitates direct peer-to-peer data transfer between the medical providers 100, 102 as described in more detail in commonly owned U.S. Pat. No. 10,257,174, entitled, "METHODS AND SYSTEMS FOR PROVIDING SECURE AND AUDITABLE TRANSFER OF ENCRYPTED DATA BETWEEN REMOTE LOCATIONS", the contents of which are hereby incorporated by reference in its entirety.

In an embodiment, the medical providers 100, 102 are, or are coupled to, a medical facility, hospital, outpatient clinic, diagnostic imaging center, diagnostic imaging station, laboratory, medical or pharmaceutical research organization, and the like. In an embodiment, the sending medical provider 100 is communicatively coupled to a picture archiving and communication system (PACS) 106. The sending medical provider 100 can be remote from, or locally coupled to, the PACS 106, and the sending medical provider 100 can be communicatively coupled to multiple local or distributed PACS (not shown). In an embodiment, the system 106 can be a health information system which contains medical imaging and related reports.

Furthermore, each of the receiving medical providers 102 are communicatively coupled to respective PACS (not shown).

In an embodiment, the medical providers 100, 102a-n are communicatively coupled to respective computing hardware and software, and can be coupled to respective databases 108, 110a-n that contain medical records, as shown in FIG. 1. In an embodiment, the medical network operator 105 can be coupled to a database 112.

In an embodiment, the database 112 can be configured to store replicated versions of data stored on the databases 108, 110. The database 112 can be updated or refreshed to reflect real-time changes to each database 108, 110, or the database 112 can be updated or refreshed on a periodic basis, such as daily, weekly, monthly, etc. In an embodiment, the database 112 can be updated or refreshed based on a triggering event, such as for example, a request for medical records being received from a sending medical provider 100 by the medical network 104.

Each database 108, 110, and 112 can be locally stored and managed by its respective associated entity, and each database 108, 110, and 112 can be distributed or cloud-based, and located remotely from its respective associated entity, such as on a remote server provided by Amazon Web Services® or the like. In an embodiment, each database 108, 110, and 112 can be a relational database, a SQL database, an object-oriented database, a centralized database, or a distributed database, such as a cloud-based database or a blockchain-based database stored across a distributed ledger. In an embodiment, the databases 108, 110 and 112 are capable of storing data and files in the DICOM format, as well as any other types of medical data, as defined herein.

In an embodiment, each medical provider 100, 102 is configured to run a respective local server 114, 116 that is operated, managed, provided, and/or developed by the medical network operator 105. In an embodiment, the local servers 114, 116 can be servers which are configured as a virtual instances of medical network server 122, and can be executed on virtual machines or virtual servers. The local servers 114, 116 can be physical, virtual, or cloud-based servers, and they can also each have a distributed server architecture. In an embodiment, the local servers 114, 116 can include DICOM standard functionality, and is configured to interface with a health information system 118, 120, such as, for example, an EHR system, RIS, VNA, and the like. The local servers 114, 116 are configured to interface with each respective health information system 118, 120 by, for example, a data exchange interface, such as the HL7 standard, the FHIR standard, the HPRIM standard, the CCR standard, the CCD specification, the xDT data exchange format, the Arden syntax, an API, direct access to a health information system, such as an EHR and/or associated databases, and the like.

In an embodiment, the sending medical provider 100 can enter a patient appointment into a patient scheduling system that is integrated with a health information system 118 such as an EHR system via a portal (i.e., such as in a FHIR interface compatible EHR or in an EHR with API access). In an embodiment, the patient appointment can be generated remotely and electronically entered or pushed into the patient scheduling system. In an embodiment, the patient scheduling system is capable of generating an appointment date for a patient.

In this embodiment, the local servers 114, 116 can leverage the data exchange interface in order to (a) obtain accurate patient demographics from a system that is considered a source of truth; and (b) enable the attachment of data that may not reside in databases 108, 110, or any other DICOM storage archive (e.g., archives or databases for laboratory testing results, prescriptions, clinical research data, and the like).

In an embodiment, each local server 114, 116 can function as an edge compute server which allows for distributed processing of data by physically being closer to each respective database 108, 110 and/or health information systems 118, 120.

In another embodiment, the functions of each local server 114, 116 can be executed by the medical network 104. In this embodiment, the medical network 104 includes a medical network server 122. In an embodiment, the medical network server 122 can be distributed across multiple computing resources within the medical network 104, or can be a dedicated computing resource.

In an embodiment, medical providers 100, 102 can be communicatively coupled to the medical network 104 via communication links (denoted by arrows in FIG. 1). These communication links may be any type of communication links suitable to allow interaction between the medical providers 100, 102, as well as with the medical network 104 and medical network operator 105. For example, the communication links may each be a wired network, a wireless network, or any combination thereof. Further, communication links may include a distributed computing network, an intranet, a local-area network (LAN) and/or a wide-area network (WAN or WLAN), or any combination thereof. For example, the LAN may make use of WIFI in its many variations and the WAN may make use of broadband, cellular and/or satellite networks using technologies including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G, 5G and LTE technologies. However, those of ordinary skill in the art will appreciate that the communication links are not limited thereto. In another embodiment, the communication links may each include ethernet, Firewire, parallel, serial, or USB connections, or short-range communication protocols such as Bluetooth, infrared, Zigbee, and the like.

In an embodiment, while the medical network 104 facilitates communication of an electronic record request between the medical providers 100, 102, the actual transmission of medical records can occur via encrypted, secure peer-to-peer communication channels 124 which have been fully described in commonly owned U.S. Pat. No. 10,257,174, entitled, "METHODS AND SYSTEMS FOR PROVIDING SECURE AND AUDITABLE TRANSFER OF ENCRYPTED DATA BETWEEN REMOTE LOCA-
TIONS", the contents of which are hereby incorporated by
reference in its entirety.

Figure 2:
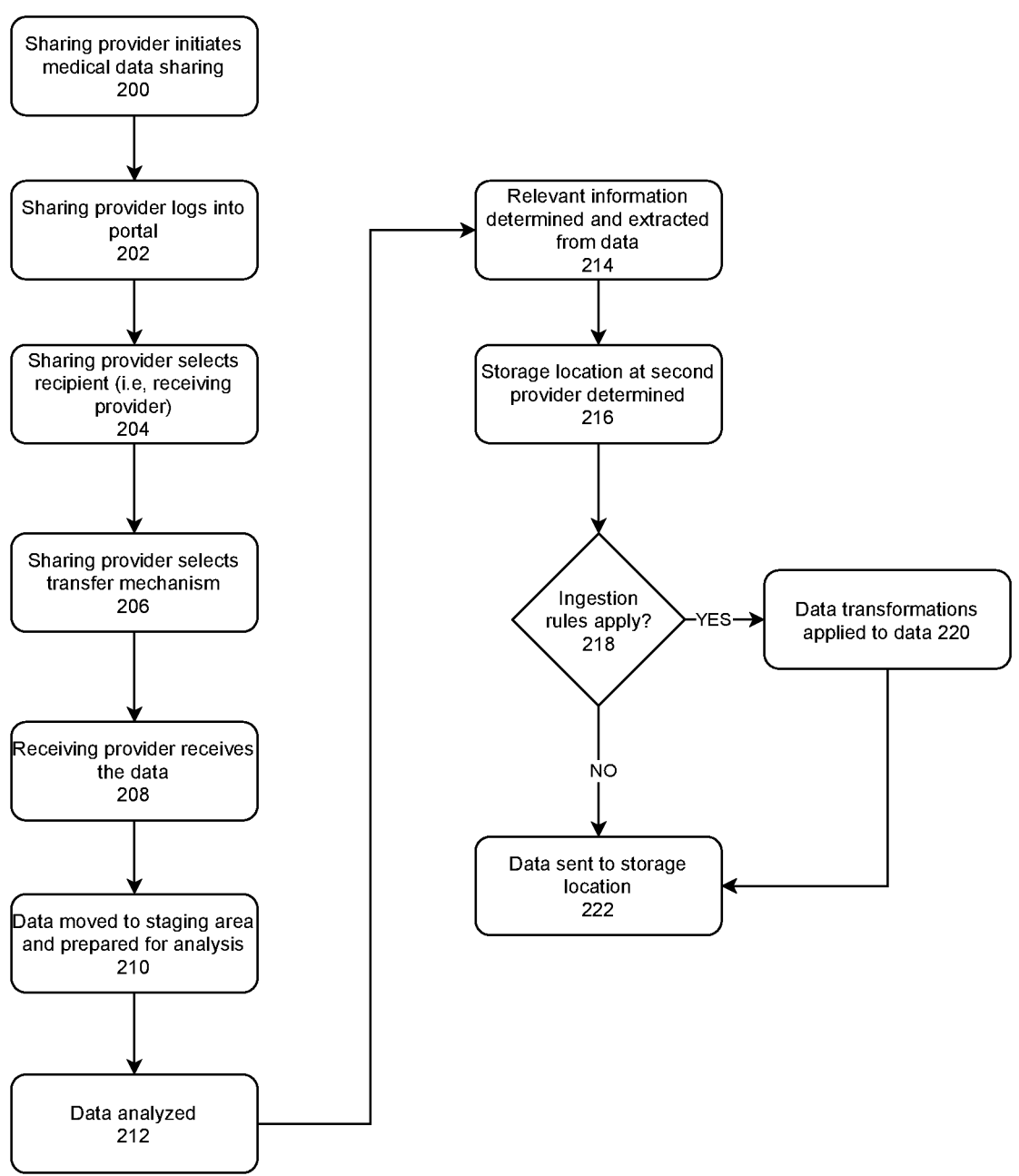
FIG. 2 is a flowchart illustrating the steps for sharing and analyzing medical data, according to an embodiment of the invention.

FIG. 2 is a flowchart illustrating the steps for sharing and
analyzing medical data, according to an embodiment of the
invention. At step 200, the sending medical provider 100
initiates a workflow to share medical data with a receiving
medical provider 102. In an embodiment, the medical data
is stored (either directly, in cached format, or in a virtual
format that utilizes pointers to a complete version of the
medical data) in a database coupled to the sending medical
provider 100, such as database 108 or database 112. In an
embodiment, the medical data is to be shared to a network
location that associated with the receiving medical provider
102, wherein the network location is communicatively
coupled to the medical network 104.

In an embodiment, the medical data exists in a document
form, such as a PDF document, Microsoft® Word document,
an Open document, an Apple® Mac page, a rich text
document, a StarOffice® document, a text document, a
Corel® WordPerfect document, a Google® document, or
any type of encapsulated document format. In another
embodiment, the medical data exists as a compressed file, a
multimedia file, an audio file, a video file, and the like. In yet
another embodiment, the medical data can exist a
Microsoft® Excel file, a comma separated values (CSV) file,
a binary text file, a spreadsheet file, a log file, or a database
file.

At step 202, the sending medical provider 100 can access
a web-based or mobile-based portal to start the process of
sharing medical data. In an embodiment, the portal can be
executed by the local server 114, and can be managed,
developed, or otherwise provided by the medical network
104 and or medical network operator 105. The portal can be
a secure website accessed via a Uniform Resource Location
(URL) using a browser on a computing device. In an
embodiment, the computing device can be a PACS station,
a medical workstation, and the like. In another embodiment,
the portal can be a downloadable software application that is
executed on a computing device, such as a mobile device,
laptop computer, desktop computer, tablet computer, smart-
phone, and the like.

In an embodiment, prior to being able to access the portal,
the medical provider must enter credentials, such as a login
and password, or other indicia that verifies their identity. The
credentials can include a user's mobile device number,
login, password, e-mail address, phone number, account
number, personal identification number (PIN), name, driv-
er's license number, social security number, date of birth,
employee number, and/or a unique account identification
code previously provided to the administrator by an autho-
rizing entity, such as an employer or the medical network
operator 105. In another embodiment, the credentials can be
biometric, such as a fingerprint, iris, facial, or voice scan. In
yet another embodiment, the credential can be a gesture
input by the user, such as a on a touchscreen or touchpad.

The portal can be stored on, or executed from, for
example, the medical network 104, the medical network
server, and/or the local servers 114, 116, and the portal
allows an administrator or staff at the medical providers 100,
102 to configure various settings and criteria for sharing
medical data, as well as permissions and privileges for other
medical providers in terms of searching, viewing, and re-
sharing medical data. The portal also allows the medical
providers 100, 102 to configure routing rules for the receipt
and reconciliation of inbound medical data.

In an embodiment, the sending medical provider 100 can
search for specific medical data that they would like to share.
For example, the portal can include an interface that allows
the sending medical provider 100 to enter a search query for
medical data based on patient demographic information. For
example, the patient demographic information can include a
patient's first, middle, and/or last name, date of birth, social
security number, sex, address, telephone number, insurance
information, primary care physician information, universal
identifier, accession number, medical record number, pro-
cedure or visit dates, and the like.

In addition, the sending medical provider 100 can search
for a specific patient's medical data by using a patient
identifier, such as a patient ID, or a procedure date or date
range, and the like, as the search query. Upon entering the
patient ID in the interface, the local server 114 can conduct
a patient-level query against the health information system
118, a DICOM archive, patient record archive, a medical
records database, and the like associated with the sending
medical provider 100. In an embodiment, the DICOM
archive can be located or communicatively coupled to the
PACS 106 and/or database 108.

In an embodiment, the sending medical provider 100 can
search for medical data based on a modality type. For
example, the sending medical provider 100 can enter a
search query for an "Mill Abdomen w/o Contrast", or
alternatively, the by simply using the terms "MM" and
"Abdomen" in the search query. Any medical data stored
with the sending medical provider 100 that is related to this
search query would be displayed on the interface for selec-
tion for sharing.

In an embodiment, the search query can include procedure
identifiers, such as, but not limited to, CPT codes, LOINC
codes, SNOMED codes, CPOE codes, procedure names,
procedure codes, insurance billing codes, procedure name
acronyms, procedure description, procedure dates, modality
types, body parts, organs, limbs and/or appendages related to
the procedure, and the like.

In this embodiment, procedure identifiers can be trans-
lated to specific modality types by the local server 114. For
example, a CPT code of "74181" is for a "MM Abdomen
w/o Contrast", while a CPT code of "75572" is for a "CT
Heart w Contrast".

In an embodiment, patient consent may be required before
the sending medical provider 100 can share a patient's
medical data. The patient consent can be completed by the
patient prior to the sending medical provider 100 starting the
process to share the medical data. In another embodiment,
the patient consent form can be automatically generated by
the local server 114 upon a determination that the sending
medical provider 100 has selected the patient's medical data
to share with a receiving medical provider 102. The patient
consent form can be transmitted to the patient for a physical
or digital signature, and can be electronically transmitted
back to the sending medical provider 100 where the com-
pleted patient consent is then stored. In the event the patient
consent form is completed via physical copy, the physical
copy can be digitized by the sending medical provider 100.

Once the sending medical provider 100 has selected the
medical data it would like to share, the sending medical
provider 100 can select the recipients at step 204. In an
embodiment, the interface allows the sending medical pro-
vider 100 select from a list of receiving medical providers
102 which are registered with the medical network 104. In
an embodiment, the sending medical provider 100 can
search for another provider by entering a provider name in
the interface. As the provider name is typed, a scrollable dropdown list can appear that is auto-populated with matching receiving medical provider names that are registered with the medical network 104.

In an embodiment, the database 112 can maintain and store a list of providers which are registered, authenticated, and/or associated with the medical network 104 and/or with the medical network operator 105.

In an embodiment, receiving medical providers 102 can restrict their ability to receive medical data, such that they are not capable of receiving any medical data, or they can choose to not receive medical data for specific patients, or from specific sending medical providers, facilities, physicians, and the like. The database 112 can further include a list of permissions and privileges which have been configured by each medical provider 100, 102.

In an embodiment, the sending medical provider 100 can select multiple receiving medical providers 102a-n to share the medical data with.

In addition, the sending medical provider 100 can specify how the medical data is shared with the receiving medical provider 102. For instance, the medical data can be shared in its native form, without any alterations or redactions, and may include personally identifying data and PHI. In addition, the sending medical provider 100 can, prior to sharing, selectively redact or scrub the medical data, can anonymize the medical data and/or deidentify the medical data. In another embodiment, the sending medical provider 100 can select multiple medical data sets and aggregate the data prior to sharing. The aggregated medical data can further be anonymized or de-identified in a batch process prior to be shared.

At step 206, the sending medical provider 100 can select a transfer mechanism for sharing the medical data with the receiving medical provider 102. The medical data can be shared using a variety of transfer mechanisms, including a push via the medical network 104, secure e-mail or direct secure messaging, electronic fax, printer driver, a hyperlink-accessed shared portal, or a phone number. Each of these transfer mechanisms is described in more detail below.

To share the medical data using a push via the medical network 104, the sending medical provider 100 logs into the portal as described herein, selects the medical data they wish to share, and selects the receiving medical provider(s) 102. The medical data is then pushed to a local server 116 coupled to the receiving medical provider 102 using the peer-to-peer communication channel 124.

To share the medical data using secure e-mail or direct secure messaging, the selected medical data can be encapsulated into a single file. The single file is attached to an encrypted e-mail and transmitted to a secure e-mail address associated with the local server 116 of the receiving medical provider 102. In an embodiment, the e-mail can be sent to the medical network 104 or medical network server 122, which can then route the e-mail to the local server 116, wherein the medical network 104 and/or medical network server 122 serve as an e-mail server. In this embodiment, the medical data, the single file, or a header or body of the e-mail includes an identifier for the receiving medical provider 102 so that the e-mail can be properly routed by the medical network 104 and/or medical network server 122.

In an embodiment, the e-mail can be a self-destructing email, in that the e-mail and attached medical data is no longer viewable or accessible to the receiving medical provider 102 after a certain time period. The time period can be set by the sending medical provider 100 or the medical network operator 105. For example, the e-mail can be deleted by the local server 116 after the time period has expired. In another embodiment, the e-mail can be a one-time access e-mail, such that the local server 116 deletes the e-mail after it has been viewed one time by the receiving medical provider 102.

Alternatively, the sending medical provider 100 can share the medical data using direct secure messaging. In this embodiment, the local servers 114, 116 can each include a data exchange network interface which facilitates direct messaging between the medical providers 100, 102.

To share the medical data via fax, the selected medical data can be encapsulated into a single file. The sending medical provider 100 faxes the single file to a fax number associated with the local server 116 of the receiving medical provider 102. In an embodiment, the fax can be sent to the medical network 104 or medical network server 122, which can then route the fax to the local server 116, wherein the medical network 104 and/or medical network server 122 serve as fax server. In this embodiment, the medical data, the single file, or a header or body of the fax must include an identifier for the receiving medical provider 102 so that the fax can be properly routed by the medical network 104 and/or medical network server 122. The fax number can be a traditional fax number or an electronic fax number.

To share the medical data via a printer driver, the selected medical data can be encapsulated into a single file, or the local server 14 can generate a printable file that contains the medical data. The sending medical provider 100 can have a printer driver associated with the medical network 104 and/or the local server 116 installed on their computing device and/or on the local server 114. In an embodiment, the printer driver is authenticated with the medical network 104 using authentication credentials associated with the sending medical provider 100 and/or the receiving medical provider 102, and is configured to print data to a print location coupled to the local server 114. In an embodiment, the print location is a file storage location where the medical data is stored as a file that is accessible by the receiving medical provider 102. In another embodiment, the print location is a physical printer or a fax machine which receives the medical data and prints the medical data to a physical medium. In yet another embodiment, the print location is an e-mail address where the medical data is printed as an e-mail.

In another embodiment, the printer driver functions as an API and provides an interface between the sending medical provider's computing device and a receiving medical provider's computing device or local server 116. The sending medical provider 100 can print the medical data at a print location associated with the local server 116.

In an embodiment, the print request can be sent to the medical network 104 or medical network server 122, which can then route the print request to the local server 116, wherein the medical network 104 and/or medical network server 122 serve as print server. In this embodiment, the medical data or the single file must include an identifier for the receiving medical provider 102 so that the print request can be properly routed by the medical network 104 and/or medical network server 122. The medical data is then routed to the print location at the local server 116 using the peer-to-peer communication channel 124.

To share the medical data via a hyperlinked-accessed shared portal, a unique hyperlink is generated by the local server 114 or medical network server 122, and transmitted to the receiving medical provider 116. The receiving medical provider 102 can access a shared portal to view the shared medical data. In an embodiment, the shared portal can utilize the same platform as the portal described herein. In another embodiment, the shared portal is a file directory listing where the receiving medical provider 102 can view and/or download the medical data.

In an embodiment, the hyperlink can be self-destructing, in that the hyperlink is no longer active or valid after a certain time period. The time period can be set by the sending medical provider 100 or the medical network operator 105. In another embodiment, the hyperlink can be a one-time access hyperlink, such that the hyperlink is disabled after the medical data has been viewed one time by the receiving medical provider 102.

To share the medical data via a phone number, the sending medical provider 100 can dial a phone number associated with the local server 116 of the receiving medical provider 102, and provide their identity as well as an authorization code for the call to be accepted by the local server 116. In an embodiment, the authorization code is generated by the medical network 104 and/or the medical network server 122. If the call is accepted by the local server 116, the sending medical provider 100 can dictate a voice message that contains medical data/information which is then transmitted to the local server 116. In this embodiment, the voice message is translated into text using speech recognition software, such as, for example, a speech-to-text converter. In an embodiment, the speech recognition software can be executed by the medical network server 122 or the local server 116, and functions to convert speech into normal language text. The converted text can then be analyzed by the local server 116 as described herein. In another embodiment, the speech recognition software can convert the speech into another language. For example, Spanish language speech can be translated and converted into English language text, and vice versa.

For the above transfer mechanisms which require an identifier for the receiving medical provider 102, if the identifier is missing, incorrect, and the like, then the medical network 104 and/or medical network server 122 rejects the shared medical data and erases or purges the shared medical data from the medical network server 122.

At step 208, the receiving medical provider 102 receives the inbound medical data from the sending medical provider 100. In an embodiment, the medical data is received by the local server 116.

At step 210, the medical data is moved to a staging area by the local server 116. The staging area can be a cache, database, or file storage location where the medical data can be temporarily stored prior to undergoing analysis. At step 212, the medical data undergoes analysis by the local server 116 in order to extract information from the medical data. In an embodiment, the medical data undergoes at least one of a natural language processing (NLP), optical character recognition (OCR), regular expression mechanisms, handwriting recognition, speech recognition, document-based data parsing, and the like, to extract information from the medical data.

For example, the local server 116 may utilize NLP to identify instances of PHI. In another example, the local server 116 can use regular expression mechanisms (also known as RegEx, RegExp, or R.E.) to identify characters and text in the medical data such as initials, geographic location coordinates, text fragments, and the like.

In an embodiment, the local server 116 can utilize machine learning to analyze medical data over time to perform identification functions more efficiently and quickly on future inbound medical data.

In another embodiment, the local server 116 can utilize NLP, OCR, regular expression mechanisms, handwriting recognition, speech recognition and/or document-based data parsing, in conjunction with machine learning analysis in order to extract information from the medical data.

At step 214, once the local server 116 identifies and extracts information from the medical data, the medical data is categorized or classified by the local server 116. In an embodiment, the extracted information is either organized using an existing mapping configuration, or is organized using machine learning into a useful format. For example, if the medical data has an identifier that explains the type of document, the local server 116 can automatically detect the document type and perform an appropriate action (i.e., a medical image and report could be routed to a PACS archive). In another example, if the medical data lacks an identifier for a type of document, the local server 116 can use machine learning to attempt to classify the document, or alternatively use a mapping configuration set by the sending medical provider 100 or the receiving medical provider 102.

In an embodiment, the document type can be included with, embedded in, appended to, or contained in the medical data, or alternatively, the document type can be included with, embedded in, appended to, or contained in the single file or printable file that is received from the sending medical provider 100.

Furthermore, if the medical data is transmitted as a single file or printable file, the local server 116 can extract the medical data, as well as identifiers, from the received file.

Furthermore, at step 214, the local server 116 utilizes identifiers in the medical data to identify relevant patient records which may be stored with the receiving medical provider 102. For example, the relevant patient information located with the receiving medical provider 102 can be identified by cross referencing the identifier extracted from the inbound medical data against database 110, as well the health information system 120 associated with the receiving medical provider 102.

At step 216, the local server 116 determines the storage location at the receiving medical provider 102 where the medical data should be routed to from the staging area. In an embodiment, the storage location can be a cache, database, or file storage location where the medical data can be temporarily or permanently stored, and can be a storage location within the health information system 120.

At step 218, the local server 118 determines if rules exist for ingesting the medical data. Such rules can be determined by, for example, the receiving medical provider 102. The rules can specify and transformations which need to be performed on the medical data prior to being stored at the storage location. For example, such transformations can include formatting the medical data in a specific fashion to be consistent with local medical data stored by the receiving medical provider 102, appending text, identifiers, or other information to the medical data, redacting information from the medical data, compressing the medical data to reduce storage size requirements, adding metadata to the medical data, removing metadata from the medical data, converting the medical data to a certain file format, and the like. For storage, the local server 116 can leverage HL7, FHIR, DICOM, SQL, direct database writing, and/or other standards and formats to store the medical data in the health information system 120.

If rules exist, then at step 220, these transformations are applied to the medical data, and then the medical data is routed to the storage location at step 220 where it is stored and made available for review, viewing, and/or listening.

If, at step 218, the local server 116 determines that rules do not exist, then the medical data is routed to the storage location at step 220 where it is stored and made available for review, viewing, and/or listening. In an embodiment, at step 220, the medical data is stored in a location different from the staging area.

While the above embodiments refer to the local server 116 as performing the functions for steps 202-222 in FIG. 2, the medical network server 122 can be utilized for some or all of these functions as well. In an embodiment, both the local server 116 and the medical network server 122 are leveraged for steps 202-222 in FIG. 2, and the medical network operator 105 can utilize load balancing algorithms in order to determine when to selectively utilize medical network server 122 if the local server 116 is experiencing high loads (i.e., due to, for example, a high number of inbound medical data streams which require simultaneous processing), and vice versa.

Clinical Decision Support

Figure 3:
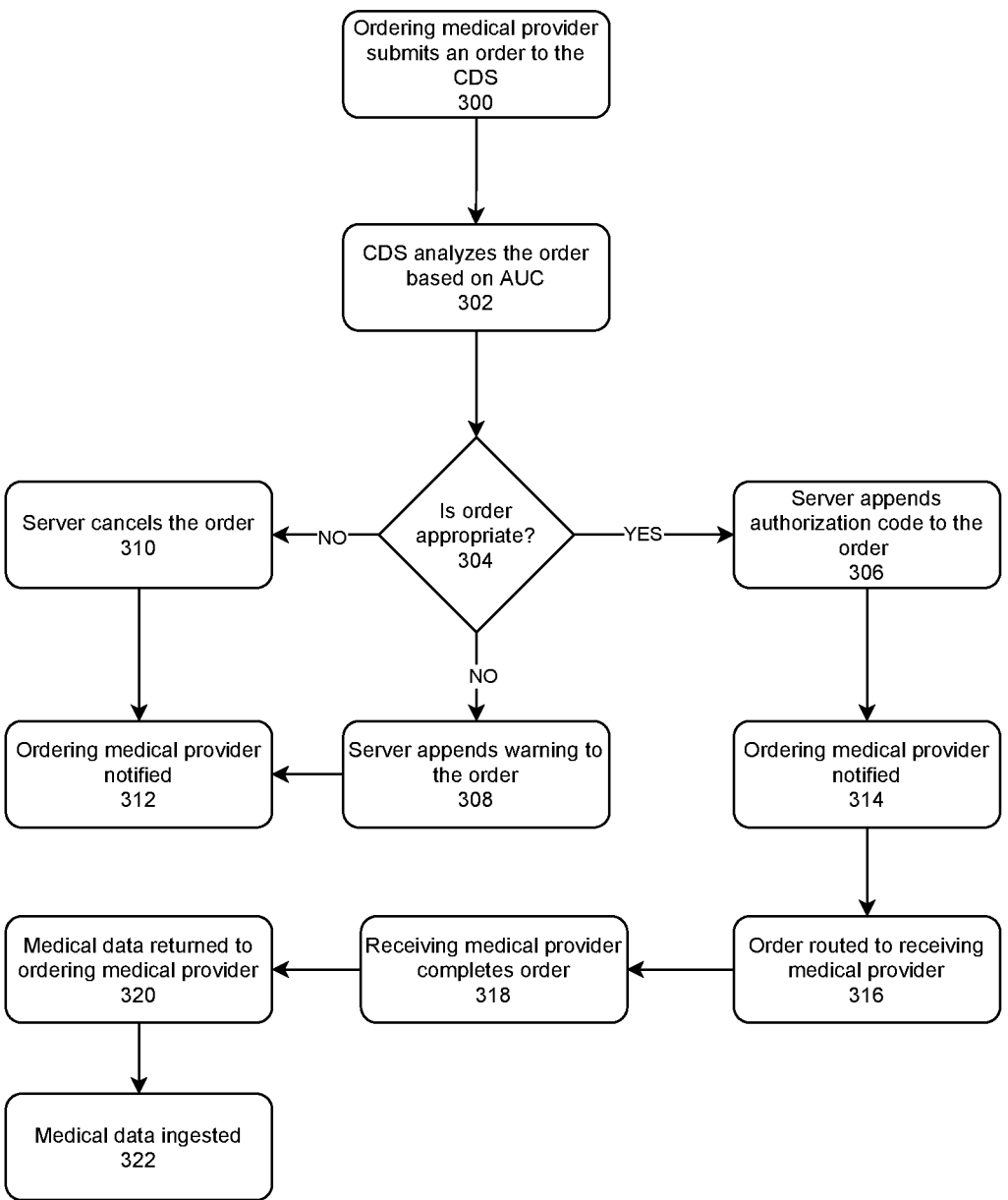
FIG. 3 is a flowchart illustrating the steps for an appropriate use assessment using clinical decision support system, according to an embodiment of the invention.

FIG. 3 is a flowchart illustrating the steps for an appropriate use assessment using a clinical decision support (CDS) system, according to an embodiment of the invention. In an embodiment, in the event that the medical data is an order for a patient examination, treatment, and/or procedure, the medical network server 122 can utilize a proprietary CDS system to ensure that the ordered procedure is appropriate for the patient. In addition, the CDS system can assist an ordering medical provider 100 (which is similar to a "sending" medical provider described herein) in receiving reimbursement for an examination, treatment, and/or procedure. In an embodiment, the CDS system can reside on the medical network server 122, or can reside on, or be executed on, a dedicated server (not shown), or on a group of distributed or cloud-based servers. In another embodiment, the CDS can be distributed across the medical network server 122 and local servers 114, 116.

At step 300, the ordering medical provider 100 submits an order to the medical network server 122. In an embodiment, the ordering medical provider 100 can have a database or list of possible orders which are mapped to a database or list of standardized orders. The standardized orders can be created by, or maintained by, the medical network operator 105, by a group of unaffiliated or affiliated medical providers, by an insurance provider, or by an industry or governmental organization, as described herein.

At step 302, the medical network server 122 analyzes the order against appropriate use criteria (AUC) (also referred to as appropriateness criteria and appropriate use guidelines). In an embodiment, the medical network server 122 can analyze an order against AUC. The AUC can be promulgated by industry and governmental organizations, such as the American Medical Association (AMA), Centers for Medicare & Medicaid Services (CMS), and the like, as well as by health insurance companies. The AUC may also include a number of aspects of the relevant clinical context that are not particular to a clinical evaluation of the patient. For example, the appropriate use guidelines may consider family history, demographics, and other such information.

In another embodiment, the medical network server 122 may utilize AUC, as well as evidence-based guidelines which may include a Care Process Model (CPM) in order to determine if a particular order is appropriate for the patient's specific indication, symptoms, and/or medical history, or if the order is inappropriate.

At step 304, the medical network server 122 determines if the ordered examination, treatment, and/or procedure is appropriate or not for the patient. If the medical network server 122 determines that the order is appropriate, then at step 306, the medical network server 122 appends an authorization code to the order.

If, however, at step 304, the medical network server 122 determines that the order is not appropriate, then at step 308, the medical network server 122 can append a warning to the order for the ordering medical provider 100. Alternatively, if the medical network server 122 determines that the order is not appropriate, then at step 310, the medical network server 122 can cancel the order and notify the ordering medical provider 100. The medical network server 122 can have pre-defined rules which dictate whether an inappropriate order is appended with a warning, or if it is to be cancelled. In an embodiment, the medical network operator 105, the ordering medical provider 100, the receiving medical provider 102, or a third-party, such as an insurance provider, can define such rules.

At step 312, if the order is not deemed appropriate in step 304, then the ordering medical provider 100 is notified of the warning that was appended in step 308, or alternatively, is notified that the order was been cancelled in step 310. In an embodiment, the medical network server 122 can notify the ordering medical provider 100 via a push via the medical network 104, secure e-mail or direct secure messaging, fax, printer driver, a hyperlink-accessed web portal, or a phone number, as described herein with respect to step 206 in FIG. 2.

In an embodiment, if the order was not cancelled by the medical network server 122 in step 310, then the ordering medical provider 100 can then decide on whether or not to continue with the order, modify the order, or cancel the order through the health information system 118, or the portal.

However, if the order is deemed appropriate in step 304, then at step 314, the ordering medical provider 100 is notified of the authorization code appeneded to the order in step 306. Similar to step 312, in step 314, the medical network server 122 can notify the medical provider 100, 102 via a push via the medical network 104, secure e-mail or direct secure messaging, fax, printer driver, a hyperlink-accessed web portal, or a phone number, as described herein with respect to step 206 in FIG. 2.

At step 316, the order is routed to a receiving medical provider 102 via a transfer mechanism as described herein with respect to step 206 in FIG. 2. In a preferred embodiment, the order is routed to the receiving medical provider 102 through a peer-to-peer communication channel 124.

At step 318, the receiving medical provider 102 completes or fulfills the order (i.e., performs the ordered examination, treatment, and/or procedure). At step 320, medical data associated with the order (i.e., examination, treatment, and/or procedure results, outcomes, notes, details, assessment, writeup, opinion, record, and the like) is returned to the ordering medical provider 100. In an embodiment, the medical data is returned to the ordering medical provider 100 via a transfer mechanism as described herein with respect to step 206 in FIG. 2. In a preferred embodiment, the medical data is returned to the ordering medical provider 100 through a peer-to-peer communication channel 124.

At step 322, the medical data is ingested by the local server 114, as described herein with respect to step 218 in FIG. 2.

In an embodiment, the medical network server 122 can leverage machine learning to analyze orders over time to more effectively and quickly perform CDS functions, as well as perform AUC assessments, on future orders. In another embodiment, the local server 114 can perform such machine learning such that the order is analyzed locally before the ordering medical provider 100 submits the order to the medical network server 122.

Treatment Decision-Making Support

In an embodiment, the CDS system can assist an ordering medical provider 100 with treatment-decision making. The ordering medical provider 100 can input their observations or notes about a patient into the health information system 118 or into the portal, and the observations can be analyzed by the medical network server 122 (i.e., via the CDS system). The medical network server 122 can utilize de-identified or anonymized medical data related to a patient's prior treatment and health history, and can leverage machine learning and artificial intelligence functions to recommend an appropriate treatment to the ordering medical provider 100. This recommendation can further be appended to a patient's medical record in the health information system 118. The ordering medical provider 100 can then use the recommendation and make a treatment decision, and then place an order which is submitted to the CDS system for an AUC assessment, as described herein with respect to step 302 in FIG. 3.

Pharmaceutical Research Support

In another embodiment, the CDS system can assist with pharmaceutical research. For example, a patient, or a medical provider 100, 102 who has obtained patient consent, can opt to automatically, or manually, share medical data and treatment outcomes with third-parties, such as pharmaceutical companies, pharmaceutical research organizations, clinical trial companies, academic institutions, and the like. Such sharing occurs via encrypted, secure peer-to-peer communication channels which are similar to peer-to-peer communication channels 124. The medical network server 122 can utilize data exchange interfaces to interface with various health information systems 118, 120 to obtain medical data related to treatment outcomes, and then deidentify or anonymize the data prior to sharing. Such information can assist pharmaceutical companies effectively and quickly collect and aggregate medical data related to side effects, efficacy, and the like from a large and diverse patient population.

In an embodiment, the patient can share on-going medical data which is captured by the patient and/or medical provider 100, 102. The on-going medical data can also be captured by a device, such as a smartwatch, fitness tracking device, wearable device, a smartphone and/or smartphone application, and the like. The on-going medical data can further assist pharmaceutical companies as described above.

Clinical Trial Qualification

In another embodiment, the invention described herein can assist with clinical trial qualification for patients. For example, when a patient check-in for an appointment, or makes a new appointment, the medical network server 122 integrated with the health information system 118, 120 via a data exchange network accesses the patient's medical data, the appointment details, and the like, to determine if the patient qualifies for a clinical trial. The medical network server 122 can leverage machine learning and artificial intelligence functions that utilize de-identified or anonymized medical data related to the patient. This medical data is then compared to qualification criteria for at least one clinical trial. In an embodiment, clinical trial qualification criteria can be transmitted to the medical network server 122, or local servers 114, 116, by third-parties which may be conducting clinical trials.

In an embodiment, if the patient qualifies for a clinical trial, the medical provider 100, 102 and/or patient is notified via a push via the medical network 104, secure e-mail or direct secure messaging, fax, printer driver, a hyperlink-accessed web portal, or a phone number, as described herein with respect to step 206 in FIG. 2. The medical provider 100, 102 can then consult with the patient and inform the patient of their qualification, as well as provide information on the clinical trial, which can be viewable through the health information systems 118, 120 or the portal described herein.

If the patient consents to participate in a clinical trial for which they qualify, the patient can be enrolled through the medical network 104, and relevant medical data for the patient can shared with the third-parties which are conducting the clinical trials via a transfer mechanism as described herein with respect to step 206 in FIG. 2. In an embodiment, the relevant medical data can be de-identified or anonymized prior to sharing, based on, for example, the nature of the clinical trial, level of patient consent, and the like.

Analytics

In an embodiment, the analysis of medical data described herein can be transmitted to the medical network 104, and stored on, for example, database 112. A plurality of medical providers 100, 102 can stream analyzed medical data in this fashion to the medical network 104. In addition, medical providers 100, 102 can connect their health information systems 118, 120 to the medical network 104 via data exchange interfaces order to stream data for reporting and analytics purposes. In an embodiment, these data connections to health information systems can augment existing data that the local servers 114, 116 may already store, such as, for example, information related to medical data and medical record transfers, orders, requests, and the like. Using a data exchange interface, the medical network operator 105 can obtain various operational information from the medical providers 100, 102, such as, for example, information related to patient wait times, addenda, re-imaging, the number of studies performed, patient engagement, patient demographics, and other service and treatment information.

For an individual medical provider 100, 102, this information can be made available in full via the portal by streaming the data through encrypted, peer-to-peer communication channel 124 between their health information system 118, 120 and the medical network server 122. If desired, the medical providers 100, 102 can elect to make this data available to other medical providers who are registered with the medical network 104, in order to provide visibility for benchmarking or research purposes. In an embodiment, the medical providers 100, 102 can also make this data available to third-parties including affordable care organizations (ACOS) for population health analytics purposes, as well as to regulatory authorities, health insurance companies, research organizations, and the like.

While the principles of the disclosure have been illustrated in relation to the exemplary embodiments shown herein, the principles of the disclosure are not limited thereto and include any modification, variation, or permutation thereof

What is claimed is:

1. A system for receiving medical data, comprising:
a data processing apparatus; and
a computer-readable medium storing instructions executable by the data processing apparatus to perform operations comprising:
establishing a connection, between the data processing apparatus and a printer driver associated with a remote medical system;
in response to establishing the connection:

receiving a printable file via the connection at a print location coupled to the data processing apparatus and associated with the printer driver, transferring the printable file to a cache coupled to the data processing apparatus;

extracting medical data from the printable file using a natural language processing algorithm and an optical character recognition algorithm, automatically detecting an identifier in the medical data, and classifying the medical data based on the identifier using a mapping configuration stored on the computer-readable medium, and determining, based on the classification, whether an ingestion rule exists for the medical data, the ingestion rule specifying one or more transformations required for storage by a receiving health information system; and in response to determining that the ingestion rule exists, transforming the medical data prior to storage in accordance with the ingestion rule, the transforming comprising at least one of modifying metadata, reformatting the medical data to a healthcare interoperability standard, or converting a file structure of the medical data; and ingesting the medical data to an appropriate database coupled to the data processing apparatus based on the classification.

2. The system of claim 1, wherein the data processing apparatus is a virtual server.

3. The system of claim 1, wherein data processing apparatus is further programmed to detect the identifier from the medical data using the natural language processing algorithm.

4. The system of claim 1, wherein the data processing apparatus is further programmed to detect the identifier from the medical data using the optical character recognition algorithm.

5. The system of claim 1, wherein the connection is an encrypted peer-to-peer communication channel.

6. The system of claim 5, wherein the encrypted peer-to-peer communication channel is terminated after the printable file has been received at the print location.

7. The system of claim 1, wherein the medical data is an order for a medical procedure.

8. A system for sharing medical data, comprising:

a data processing apparatus; and a computer-readable medium storing instructions executable by the data processing apparatus to perform operations comprising:

establishing a connection, between the data processing apparatus and a printer driver associated with a remote medical system;

in response to establishing the connection:

receiving a printable file via the connection at a print location coupled to the data processing apparatus and associated with the printer driver, transferring the printable file to a cache coupled to the data processing apparatus, extracting medical data from the printable file using a natural language processing algorithm and an optical character recognition algorithm, automatically detecting a document type of the medical data, and determining a classification of the medical data using a machine learning algorithm stored on the computer-readable medium, the document type classifying the type of medical data;

determining, based on the classification, whether an ingestion rule exists for the medical data, the ingestion rule specifying one or more transformations required for storage by a receiving health information system; and in response to determining that the ingestion rule exists, automatically transforming the medical data prior to storage in accordance with the ingestion rule, the transforming comprising at least one of modifying metadata, reformatting the medical data to a healthcare interoperability standard, or converting a file structure of the medical data; and routing the transformed medical data to an appropriate database coupled to the data processing apparatus based on the classification.

9. The system of claim 8, wherein the data processing apparatus is a virtual server.

10. The system of claim 8, wherein data processing apparatus is further programmed to detect the identifier from the medical data using the natural language processing algorithm.

11. The system of claim 8, wherein the data processing apparatus is further programmed to detect the identifier from the medical data using the optical character recognition algorithm.

12. The system of claim 8, wherein the connection is an encrypted peer-to-peer communication channel.

13. The system of claim 12, wherein the encrypted peer-to-peer communication channel is terminated after the printable file has been received at the print location.

14. The system of claim 8, wherein the data processing apparatus is further programmed to extract the medical data using handwriting recognition.

15. A system for sharing medical data, comprising:

a data processing apparatus; and a computer-readable medium storing instructions executable by the data processing apparatus to perform operations comprising:

establishing a connection, between the data processing apparatus and a printer driver associated with a remote medical system;

in response to establishing the connection:

receiving a printable file via the connection at a print location coupled to the data processing apparatus and associated with the printer driver, transferring the printable file to a cache coupled to the data processing apparatus, extracting medical data from the printable file using a natural language processing algorithm and an optical character recognition algorithm, automatically detecting a document type of the medical data, and classifying the medical data based on the document type using a mapping configuration stored on the computer-readable medium, and determining whether an ingestion rule exists for the classified medical data, the ingestion rule defining one or more data transformations required by a receiving health information system; and in response to determining that the ingestion rule exists, transforming the medical data, transforming the medical data prior to ingestion in accordance with the ingestion rule; and

ingesting the medical data to an appropriate database coupled to the data processing apparatus based on the classification.

16. The system of claim 15, wherein the document type is embedded within the medical data.

17. The system of claim 15, wherein the connection is an encrypted peer-to-peer communication channel.

18. The system of claim 17, wherein the encrypted peer-to-peer communication channel is terminated after the printable file has been received at the print location.

19. The system of claim 15, wherein the data processing apparatus is further programmed to extract the medical data using handwriting recognition.

20. The system of claim 15, wherein transforming the medical data prior to ingestion comprises formatting the medical data in accordance with a healthcare interoperability standard selected from HL7, FHIR, or DICOM.

\* \* \* \* \*